United States Patent
Breton

(10) Patent No.: US 6,852,326 B2
(45) Date of Patent: *Feb. 8, 2005

(54) COMPOSITION, IN PARTICULAR COSMETIC, CONTAINING 7-HYDROXY DHEA AND/OR 7-KETO DHEA AND AT LEAST AN ISOFLAVONOID

(75) Inventor: Lionel Breton, Versailles (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/433,489

(22) PCT Filed: Nov. 20, 2001

(86) PCT No.: PCT/FR01/03642

§ 371 (c)(1), (2), (4) Date: Nov. 5, 2003

(87) PCT Pub. No.: WO02/47631

PCT Pub. Date: Jun. 20, 2002

(65) Prior Publication Data

US 2004/0072764 A1 Apr. 15, 2004

(30) Foreign Application Priority Data

Dec. 15, 2000 (FR) .............................................. 00 16432

(51) Int. Cl.⁷ ............................ A61K 7/00; A61K 7/42; A61K 7/44; A61K 35/78
(52) U.S. Cl. ......................... 424/401; 424/59; 424/69; 424/400; 424/725
(58) Field of Search ........................... 424/59, 60, 400, 424/401, 725

(56) References Cited

U.S. PATENT DOCUMENTS

| | | |
|---|---|---|
| 6,048,846 A | 4/2000 | Cochran |
| 6,093,706 A | 7/2000 | Zeligs |
| 6,121,243 A * | 9/2000 | Lanzendorfer et al. ....... 514/28 |
| 2004/0077722 A1 | 4/2004 | Breton |

FOREIGN PATENT DOCUMENTS

| | | |
|---|---|---|
| DE | 44 32 947 | 3/1996 |
| DE | 44 32 947 A1 | 3/1996 |
| EP | 0 908 183 | 4/1999 |
| EP | 0 908 183 A1 | 4/1999 |
| FR | 2 765 803 | 1/1999 |
| FR | 2 765 803 A1 | 1/1999 |
| FR | 2 771 105 | 5/1999 |
| FR | 2 777 182 | 10/1999 |
| FR | 2 777 182 A1 | 10/1999 |
| WO | WO 92/03925 | 3/1992 |
| WO | 92 03925 | 3/1992 |
| WO | WO 97/03676 | 2/1997 |
| WO | 97 03676 | 2/1997 |
| WO | WO 9803170 | 1/1998 |
| WO | 98 40074 | 9/1998 |
| WO | WO 98/40074 | 9/1998 |
| WO | WO 98/56373 | 12/1998 |
| WO | 98 56373 | 12/1998 |
| WO | WO 99/07381 | 2/1999 |
| WO | 99 07381 | 2/1999 |
| WO | WO 00/01351 | 1/2000 |
| WO | 00 01351 | 1/2000 |
| WO | 00 28996 | 5/2000 |
| WO | WO 00/28996 | 5/2000 |

* cited by examiner

Primary Examiner—Shelley A. Dodson
(74) Attorney, Agent, or Firm—Oblon, Spivak, McClelland, Maier & Neustadt, P.C.

(57) ABSTRACT

The invention concerns a composition containing, in a physiologically acceptable medium: (a) at least a DHEA derivative selected among 7-hydroxy DHEA and 7-keto DHEA, and (b) at least an isoflavonoid. The invention also concerns cosmetic and dermatological uses of said composition, in particular for preventing or treating actinic skin ageing symptoms.

23 Claims, No Drawings

COMPOSITION, IN PARTICULAR COSMETIC, CONTAINING 7-HYDROXY DHEA AND/OR 7-KETO DHEA AND AT LEAST AN ISOFLAVONOID

The present invention relates to a composition containing 7-hydroxy-DHEA and/or 7-keto-DHEA and at least one isoflavonoid, and to the use of said composition, in particular for preventing or treating the signs of actinic skin aging.

DHEA, or dehydroepiandrosterone, is a natural steroid which is mainly produced by the corticoadrenal glands. Exogenous DHEA, administered topically or orally, is known for its capacity to promote keratinization of the epidermis (JP-07 196 467) and to treat dry skins by increasing the endogenous production and the secretion of sebum and by thus reinforcing the barrier effect of the skin (U.S. Pat. No. 4,496,556). There has also been described in patent U.S. Pat. No. 5,843,932 the use of DHEA for treating atrophy of the dermis by inhibiting the loss of collagen and of connective tissue. Finally, the applicant has demonstrated the capacity of DHEA to control the weathered appearance of the skin (FR 00/00349), and to modulate the pigmentation of the skin and of the hair (FR 99/12773) and to control atrophy of the epidermis (FR 00/06154). These properties of DHEA make it a candidate of choice as anti-aging active agent.

Among the metabolites of DHEA, particular attention has been made in the last few years to 7α-hydroxy-DHEA. It has indeed been demonstrated that this metabolite, which does not possess the hormonal activity of DHEA, made it possible to increase the proliferation of the fibroblasts and the viability of the human keratinocytes and had anti-free radical effects (WO 98/40074). It has also been demonstrated, on rats (WO 00/28996), that 7α-hydroxy-DHEA increased the thickness of the dermis and the elastin and collagen content of the skin. It has thus been suggested to use this metabolite of DHEA for preventing and/or treating the harmful effects of UV radiation on the skin, for controlling wrinkles and for increasing skin firmness and tone.

7α-Hydroxy-DHEA is, with 5-androstene-3β, 17β-diol, a major metabolite of DHEA, which is obtained by the action of 7α-hydroxylase on DHEA. Among the minor metabolites of DHEA, there may be mentioned 7β-hydroxy-DHEA, which is obtained by the action of 7β-hydroxylase on DHEA and 7-keto-DHEA, which is itself a metabolite of 7β-hydroxy-DHEA.

In the remainder of this description, the expression "7-hydroxy-DHEA" will be used to designate without distinction 7α-hydroxy-DHEA and 7β-hydroxy-DHEA.

It is now evident to the applicant that the combination of 7-hydroxy-DHEA and/or 7-keto-DHEA with an isoflavonoid could make it possible to more effectively prevent or treat the signs of skin aging, in particular of actinic aging or photoaging.

The subject of the present invention is therefore a composition containing, in a physiologically acceptable medium: (a) at least one DHEA derivative chosen from 7-hydroxy-DHEA and 7-keto-DHEA, and (b) at least one isoflavonoid.

7-Hydroxy-DHEA is preferably 7α-OH-DHEA. A method for preparing this compound is described in particular in Patent Applications FR-2 771 105 and WO 94/08588. However, 7β-OH-DHEA is also suitable for use in the present invention.

The concentration of DHEA derivative in the composition according to the invention is advantageously between 0.0000001% and 10% by weight, preferably between 0.00001% and 5% by weight, relative to the total weight of the composition.

The composition according to the present invention contains, in combination with the DHEA derivative, at least one isoflavonoid.

Isoflavonoids constitute a subclass of flavonoids, consisting of a 3-phenylchroman backbone which may contain various substituents and different levels of oxidation. Unlike flavonoids, they are only present in a very limited number of plants.

The term isoflavonoid covers several classes of compounds among which there may be mentioned isoflavones, isoflavanones, rotenoids, pterocarpans, isoflavans, isoflavan-3-enes, 3-arylcoumarins, 3-aryl-4-hydroxycoumarins, coumestans, coumaronochromones or 2-arylbenzofurans. In this regard, reference may be advantageously made, for a complete review of isoflavonoids, their methods of analysis and their sources, to chapter 5 "Isoflavonoids", written by P. M. Dewick, in *The Flavonoids*, publisher Harbone, pp. 125–157 (1988).

The isoflavonoids which are suitable for use in the present invention may be of natural or synthetic origin. The expression "natural origin" is understood to mean the isoflavonoid, in the pure state or in solution at various concentrations, obtained by various methods of extraction from a component, generally a plant, of natural origin. The expression "synthetic origin" is understood to mean the isoflavonoid, in the pure state or in solution at various concentrations, obtained by chemical synthesis.

It is preferable to use isoflavonoids of natural origin. Among these, there may be mentioned: daidzin, genistin, daidzein, formononetin, cuneatin, genistein, isoprunetin and prunetin, cajanin, orobol, pratensein, santal, junipegenin A, glycitein, afrormosin, retusin, tectorigenin, irisolidone, jamaicin, and their analogs and metabolites.

The isoflavonoid preferably represents from $10^{-10}$% to 10%, and preferably from $10^{-8}$ to 5%, of the total weight of the composition. Of course, if the isoflavonoid is present in the form of a solution containing a plant extract, persons skilled in the art will know how to adjust the quantity of this solution in the composition according to the invention so as to obtain the above isoflavonoid concentration ranges.

The isoflavones are preferred for use in the present invention. This term is understood to mean both the aglycone forms (daidzein, genistein, glycitein) and the glycosylated forms (daidzin, genistin, glycitin) of the isoflavones.

Methods for preparing isoflavones are described in particular in WO 95/10530, WO 95/10512, U.S. Pat. No. 5,679,806, U.S. Pat. No. 5,554,519, EP-812 837 and WO 97/26269.

However, for use in the present invention, it is preferable to use the isoflavones in the form of soybean extracts marketed by ICHIMARU PHARCOS under the trade name Flavosterone SB® and by ARCHER DANIELS MIDLAND COMPANY under the trade name Novasoy®. These extracts predominantly contain isoflavones in glycosylated form, which can be metabolized in the body to their aglycone forms, and aglycone isoflavones as minor components.

Isoflavones are in particular known as antioxidants, for their anti-free radical and depigmenting properties, and for inhibiting the activity of the sebaceous glands (see in particular DE-44 32 947). They have also been described as agents for preventing the signs of skin aging, including flabby skin and the loss of radiance of the complexion (JP 1-96106).

It will therefore be appreciated that the combination of a DHEA derivative as defined above with isoflavonoids makes it possible to reinforce the anti-aging effects of the composition containing them, in particular when this involves preventing or treating the signs of actinic skin aging.

The composition according to the invention is preferably suitable for topical application to the skin. It may be provided in all the galenic forms normally used for this type of application, in particular in the form of an aqueous or oily solution, an oil-in-water or water-in-oil or multiple emulsion, a silicone emulsion, a microemulsion or nanoemulsion, an aqueous or oily gel or a liquid, pasty or solid anhydrous product.

This composition may be fluid to a greater or lesser degree and may have the appearance of a white or colored cream, an ointment, a milk, a lotion, a serum, a paste, a mousse or a gel. It may be optionally applied to the skin in aerosol form. It may also be provided in solid form, for example in the form of a stick. It may be used as a care product and/or as a make-up product for the skin.

In a known manner, the composition of the invention may also contain the customary adjuvants in the cosmetic and dermatological fields, such as hydrophilic or lipophilic gelling agents, hydrophilic or lipophilic active agents, preservatives, antioxidants, solvents, perfumes, fillers, screening agents, pigments, odor absorbers and coloring matter. The quantities of these various adjuvants are those conventionally used in the fields considered, and are for example from 0.01 to 20% of the total weight of the composition. These adjuvants, depending on their nature, can be introduced into the fatty phase or into the aqueous phase. These adjuvants, and their concentrations, should be such that they do not adversely affect the advantageous properties of the DHEA derivatives, or of the isoflavonoids according to the invention.

When the composition according to the invention is an emulsion, the proportion of the fatty phase may range from 5 to 80% by weight, and preferably from 5 to 50% by weight relative to the total weight of the composition. The fatty substances, the emulsifiers and the coemulsifiers used in the composition in the form of an emulsion are chosen from those conventionally used in the field considered. The emulsifier and the coemulsifier are preferably present in the composition in a proportion ranging from 0.3 to 30% by weight, and preferably from 0.5 to 20% by weight relative to the total weight of the composition.

As fatty substances which can be used in the invention, it is possible to use oils and in particular mineral oils (liquid paraffin), oils of plant origin (avocado oil, soybean oil), oils of animal origin (lanolin), synthetic oils (perhydrosqualene), silicone oils (cyclomethicone) and fluorinated oils (perfluoro-polyethers). It is also possible to use, as fatty substances, fatty alcohols such as cetyl alcohol, fatty acids, waxes and gums, and in particular silicone gums.

As emulsifiers and coemulsifiers which can be used in the invention, there may be mentioned, for example, esters of fatty acids and of polyethylene glycol such as PEG-100 stearate, PEG-50 stearate and PEG-40 stearate; esters of fatty acids and of polyols such as glyceryl stearate, sorbitan tristearate, oxyethylenated sorbitan stearates which are available under the trade names Tween® 20 or Tween® 60, for example; and mixtures thereof.

As hydrophilic gelling agents, there may be mentioned in particular carboxyvinyl polymers (carbomer), acrylic copolymers such as acrylate/alkyl acrylate copolymers, polyacrylamides, polysaccharides, natural gums and clays, and, as lipophilic gelling agents, there may be mentioned modified clays such as bentones, metal salts of fatty acids and hydrophobic silica.

According to one variant of the invention, the composition may be suitable for administration by the oral route. In this case, it may be provided in the form of syrups, suspensions, solutions, emulsions, granules, capsules or tablets, for example.

The daily doses of DHEA derivative which are administered by the oral route may be between 1 and 100 mg/day, preferably between 25 and 75 mg/day. Preferably, the DHEA derivative is present in the composition according to the invention in a quantity allowing its administration at a dose between 50 and 100 mg/day, said dosage being obtained in one or more doses, with a unit dose of 50 mg.

The daily doses of isoflavonoids administered by the oral route should be defined on a case by case basis, in order to obtain the desired physiological effect. More particularly, in the case of isoflavones, alone or in an extract, the daily isoflavone doses may be between 0.1 and 500 mg/day. Preferably, the isoflavones are present in the composition according to the invention in a quantity allowing its administration at a dose between 10 and 300 mg/day. Said dosage being obtained in one or more doses.

In all cases, the composition according to the invention and/or the preparation obtained therefrom comprises an effective quantity of DHEA derivative and an effective quantity of isoflavonoid, sufficient to obtain the desired effect, in a physiologically acceptable medium.

The composition according to the invention finds application in particular in the prevention and treatment of the signs of skin aging, in particular of actinic aging.

The present invention therefore also relates to the cosmetic use of the abovementioned composition for the prevention or treatment of the signs of skin aging, in particular of actinic aging.

It relates in particular to the cosmetic use of the composition described above for preventing or controlling the formation of wrinkles and/or for improving skin tone and/or for increasing skin firmness.

The present invention also relates to the cosmetic use of the composition described above for preventing or controlling the harmful effects of UV radiation on the skin.

It finally relates to the use of the composition described above for manufacturing a preparation intended for preventing or controlling the harmful effects of UV radiation on the skin.

The invention will now be illustrated by the following nonlimiting examples. In these examples, the quantities are indicated as a percentage by weight.

EXAMPLE 1

Composition Topical Application

| Phase A1 | |
|---|---|
| 2-Octyldodecanol | 20% |
| 7α-OH-DHEA | 1% |
| Phase A2 | |
| Polyglyceryl distearate (2 mol) | 2% |
| PEG monostearate (8 EO) | 1.35% |
| Stearic acid | 1% |
| Preservative | 0.1% |
| Phase B | |
| Preservatives | 0.35% |
| Neutralizing agents | 0.25% |
| Propylene glycol | 5% |

-continued

| | |
|---|---|
| Soybean aqueous extract containing 0.2% of isoflavones and 30% of butylene glycol (Flavosterone SB - ICHIMARU PHARCOS) | 5% |
| Water | qs 100% |
| Phase C | |
| Gelling agent | 0.5% |
| Neutralizing agent | 0.2% |
| Water | qs |

This composition may be prepared in the following manner: phases A1, A2 and B are prepared separately by mixing their constituents in the hot state, with stirring. Phases A1 and A2 are mixed in the hot state, and then phase B is added to them. After cooling to room temperature, phase C is added to the mixture thus obtained.

This composition may be used as twice-daily applications for preventing or treating the signs of skin aging such as wrinkles and flabby skin.

EXAMPLE 2

Composition for Oral Administration

Soft gelatin capsules having the following composition are prepared in a manner which is conventional for persons skilled in the art:

| | |
|---|---|
| Hydrogenated soybean oil | 40 mg |
| Wheat oil | 95 mg |
| Soybean lecithin | 20 mg |
| Natural tocopherols | 5 mg |
| Soybean extract available under the name Novasoy ® from AMD (corresponding to approximately 50 mg of isoflavones) | 120 mg |
| 7α-OH-DHEA | 50 mg |

What is claimed is:

1. A composition comprising:
   a physiologically acceptable medium;
   at least one DHEA derivative selected from the group consisting of 7-hydroxy-DHEA and 7-keto-DHEA; and
   at least one isoflavonoid.

2. The composition as claimed in claim 1, comprising 7α-OH-DHEA.

3. The composition as claimed in claim 1, comprising 7β-OH-DHEA.

4. The composition as claimed in claim 1, wherein said isoflavonoid is a natural isoflavonoid.

5. The composition as claimed in claim 4, wherein said isoflavonoid is an isoflavones.

6. The composition as claimed in claim 1, wherein said isoflavonoid is selected from the group consisting of daidzin, genistin, daidzein, formononetin, cuneatin, genistein, isoprunetin, prunetin, cajanin, orobol, pratensein, santal, junipegenin A, glycitein, afrormosin, retusin, tectorigenin, irisolidone, jamaicin, analogs thereof and metabolites thereof.

7. The composition as claimed in claim 1, wherein said isoflavonoid is selected from the group consisting of daidzein, genistein, glycitein, daidzin, genistin and glycitin.

8. The composition as claimed in 1, wherein said composition is for topical application to the skin.

9. The composition as claimed in claim 1, wherein said DHEA derivative is present in an amount of from 0.0000001 to 10% by weight, relative to the total weight of the composition.

10. The composition as claimed in claim 1, wherein said DHEA derivative is present in an amount of from 0.00001 to 5% by weight, relative to the total weight of the composition.

11. The composition as claimed in claim 1, wherein the isoflavanoid is present in an amount of from $10^{-10}$% to 10% by weight, relative to the total weight of the composition.

12. The composition as claimed in claim 1, wherein the isoflavanoid is present in an amount of from $10^{-8}$% to 5% by weight, relative to the total weight of the composition.

13. The composition as claimed in claim 1 wherein the composition is for administration by the oral route.

14. A process comprising:
    applying the composition of claim 1 to the skin of a human.

15. A process comprising:
    applying the composition of claim 1 to the skin of a human in an amount effective for preventing the formation of wrinkles.

16. A process comprising:
    applying the composition of claim 1 to the skin of a human in an amount effective for controlling the formation of wrinkles.

17. A process comprising:
    applying the composition of claim 1 the skin of a human in an amount effective for increasing skin firmness.

18. A process comprising:
    applying the composition of claim 1 to the skin of a human in an amount effective for preventing the harmful effects of UV radiation on the skin of a human.

19. A process comprising:
    applying the composition of claim 1 to the skin of a human in an amount effective for controlling the harmful effects of UV radiation on the skin of a human.

20. A process comprising:
    applying the composition of claim 1 to the skin of a human in an amount effective for preventing the signs of skin aging.

21. A process comprising:
    applying the composition of claim 1 to the skin of a human in an amount effective for controlling the signs of skin aging.

22. A process comprising:
    applying the composition of claim 1 to the skin of a human in an amount effective for preventing the signs of actinic aging.

23. A process comprising:
    applying the composition of claim 1 to the skin of a human in an amount effective for treating the signs of actinic aging.

* * * * *

UNITED STATES PATENT AND TRADEMARK OFFICE
CERTIFICATE OF CORRECTION

PATENT NO.   : 6,852,326 B2
DATED        : February 8, 2005
INVENTOR(S)  : Lionel Breton It is certified that error appears in the above-identified patent and that said Letters Patent is hereby corrected as shown below:

Title page,
Item [57], ABSTRACT,
Line 7, change "ageing" to -- aging --.

Column 5,
Line 51, "isoflavones" should be -- isoflavone --.

Column 6,
Line 33, "claim 1 the skin" should read -- claim 1 to the skin --.

Signed and Sealed this

Seventeenth Day of May, 2005

JON W. DUDAS
*Director of the United States Patent and Trademark Office*